US012558680B1

(12) United States Patent
Nambyaruveettil et al.

(10) Patent No.: US 12,558,680 B1
(45) Date of Patent: Feb. 24, 2026

(54) HYBRID-SUPPORTED CATALYST, METHOD OF PREPARING THEREOF, AND APPLICATION(S) THEREOF

(71) Applicant: United Arab Emirates University, Al Ain (AE)

(72) Inventors: Suryamol Nambyaruveettil, Al Ain (AE); Labeeb Ali, Al Ain (AE); Mohammednoor Al Tarawneh, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 19/055,967

(22) Filed: Feb. 18, 2025

(51) Int. Cl.
| | |
|---|---|
| *B01J 37/08* | (2006.01) |
| *B01J 35/00* | (2024.01) |
| *B01J 35/45* | (2024.01) |
| *B01J 35/63* | (2024.01) |
| *B01J 37/04* | (2006.01) |
| *C07C 5/05* | (2006.01) |

(52) U.S. Cl.
CPC .............. *B01J 37/08* (2013.01); *B01J 35/19* (2024.01); *B01J 35/45* (2024.01); *B01J 35/633* (2024.01); *B01J 37/04* (2013.01); *C07C 5/05* (2013.01); *C07C 2523/755* (2013.01)

(58) Field of Classification Search
CPC ... B01J 37/08; B01J 37/04; B01J 35/45; B01J 35/633; C07C 5/05
See application file for complete search history.

(56) References Cited

PUBLICATIONS

Wang et al., Fuel, (2021), v.293, p. 120426 (1-10).*
Wang et al., Int. Journal of Hydrogen Energy, (2024), v.69, p. 532-548.*
Acevedo-Paez et al., Int. Journal of Hydrogen Energy, (2024), v.52, p. 1248-1262.*
Elanthikkal et al., Arabian Journal of Chemistry, (2023), v.16, p. 104522(1-13).*

* cited by examiner

*Primary Examiner* — Yong L Chu

(74) *Attorney, Agent, or Firm* — MH2 Technology Law Group, LLP

(57) ABSTRACT

The present disclosure belongs to the technical field of catalysts. In particular, the present disclosure relates to a hybrid-supported catalyst and a process for preparing the hybrid supported catalyst. The hybrid-supported catalyst comprises a hybrid support and a hydrogenation catalyst dispersed on the hybrid-support. The hybrid support comprises silica containing material and a biochar. The present disclosure also provides a method for hydrogenation of unsaturated hydrocarbon in the presence of the hybrid-supported catalyst.

19 Claims, 6 Drawing Sheets

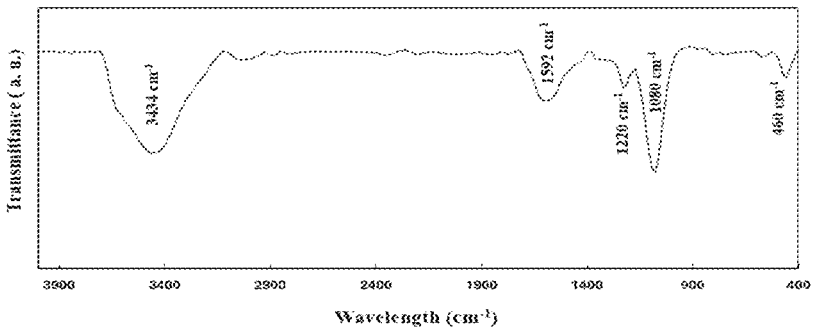
Fig. 7
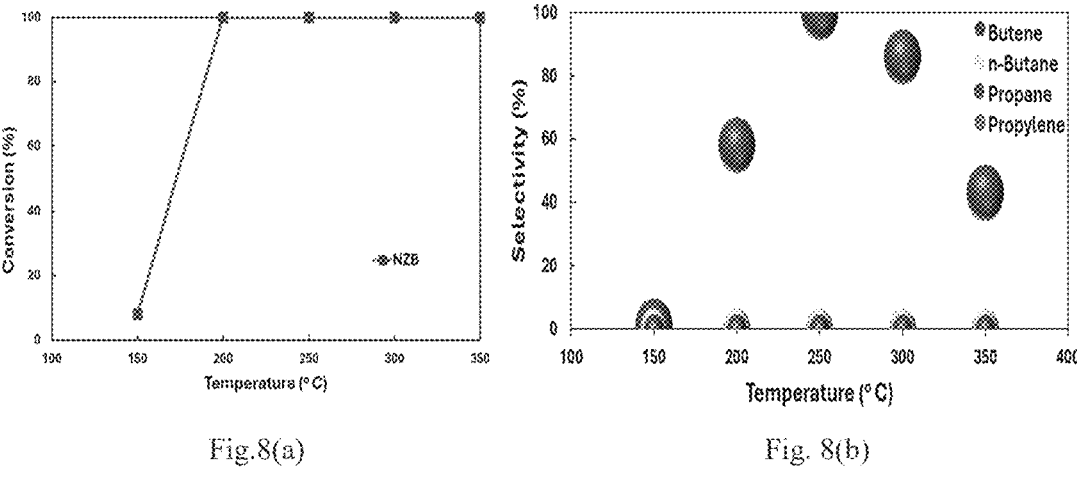
Fig.8(a)                    Fig. 8(b)

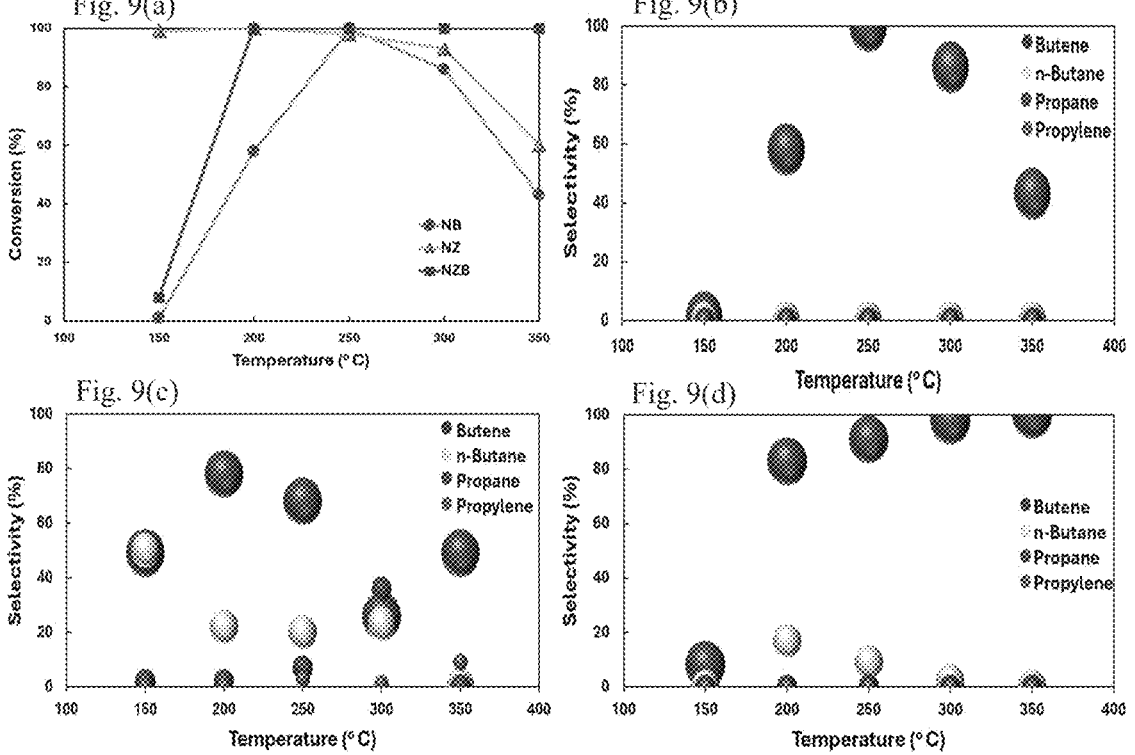

1. H2 gas
2. BD gas
3. Mass flow Controller (MFC)
4. MFC
5. MFC
6. Vertical flow reactor
7. Electric furnace
8. Catalyst
9. Quartz wool
10. GC-MS

1

HYBRID-SUPPORTED CATALYST, METHOD OF PREPARING THEREOF, AND APPLICATION(S) THEREOF

TECHNICAL FIELD

The present disclosure belongs to the technical field of catalysts. In particular, the present disclosure relates to a hybrid-supported catalyst and a process for preparing thereof. More particularly, the present disclosure relates to a biochar-based hybrid-supported catalyst and a process for preparing thereof. Further, the present disclosure provides a method for selective hydrogenation of unsaturated hydrocarbons such as butadiene in the presence of the hybrid-supported catalyst.

BACKGROUND

Catalytic hydrogenation is a crucial process in the petrochemical industry, particularly for converting unsaturated hydrocarbons like butadiene into more stable and valuable products. The hydrogenated products of butadiene comprise 1-butene, cis-2-butene, trans-2-butene and butane. Among them, 1-butene has the highest added value. Conventional catalysts for selective hydrogenation of the butadiene to olefin, particularly for 1-butene, while producing little or no butane, typically use metals such as nickel, palladium, platinum, or gold solid supports.

However, these conventional catalysts often suffer from rapid deactivation, necessitating frequent replacement of catalysts, which increases operational costs. Further, the hydrogenation of butadiene using these catalysts typically requires high temperatures, consuming significant energy and high hydrogen to hydrocarbon ratio. Furthermore, existing conventional catalysts struggle to achieve complete conversion, leaving unreacted butadiene. Thus, the conventional catalysts face challenges including rapid deactivation, high energy requirements, and/or incomplete conversion rates. Furthermore, many advanced catalysts face challenges in scaling up from laboratory to industrial scales.

Thus, there remains a need for an energy efficient, environmentally friendly, deactivation resistant and/or cost-effective hybrid-supported catalyst with improved catalytic activity to improve productivity in a desired range of product distribution, specifically butene.

SUMMARY

In one aspect, the present disclosure provides a hybrid-supported catalyst, comprising:
a hybrid support comprising a silica containing material and a biochar; and
a hydrogenation catalyst dispersed on the hybrid support.

In another aspect, the present disclosure provides a hybrid-supported catalyst, comprising: a hybrid support comprising a silica containing material and biochar derived from without limitation one or more materials selected from the group consisting of date pit(s), date pit(s) waste, corn cobs, sawdust, wood chips, crop stalks, husks, straw, and any combination thereof; and a hydrogenation catalyst dispersed on the hybrid support.

In another aspect, the present disclosure provides a hybrid-supported catalyst, comprising: a hybrid support comprising a silica containing material and aa biochar derived from date pit(s), and/or date pit(s) waste; and a hydrogenation catalyst dispersed on the hybrid support.

In another aspect, the present disclosure provides a hybrid-supported catalyst for selective hydrogenation of unsaturated hydrocarbon.

In another aspect, the present disclosure provides a hybrid-supported catalyst for selective hydrogenation of butadiene to 1-butene with at least 99% yield.

In another aspect, the present disclosure provides a method for preparing a hybrid-supported catalyst comprising the steps of adding a solution comprising a hydrogenation catalyst to a biochar to get a suspension; adding a solution of a silica containing material to the suspension with constant stirring to obtain a wet hybrid-supported catalyst; drying the wet hybrid-supported catalyst; and then calcining the dried hybrid-supported catalyst.

In yet another aspect, the present disclosure provides a method for hydrogenation of an unsaturated hydrocarbon, comprising contacting the unsaturated hydrocarbon with hydrogen in the presence of a hybrid-supported catalyst.

In yet another aspect, the present disclosure provides a process for producing butene, comprising contacting butadiene with a hybrid-supported catalyst as defined in any of the preceding aspects.

BRIEF DESCRIPTION OF ACCOMPANYING DRAWINGS

The accompanying drawings, which are incorporated in and constitute a part of this disclosure, illustrate exemplary embodiments and together with the description, serve to explain the disclosed principles. The present disclosure will now be described with the help of an accompanying diagram, in which FIG. 1 illustrates the Scanning Electron Microscopy (SEM) & Energy Dispersive X-ray Spectroscopy (EDS) mapping of hybrid-supported catalyst as per the present disclosure (Example 3).

FIG. 5($a$) and FIG. 5($b$) illustrate the Temperature Programmed Oxidation (TPO) of hybrid-supported catalyst as per the present disclosure (Example 3) before and after the reaction, respectively.

Figure 6:
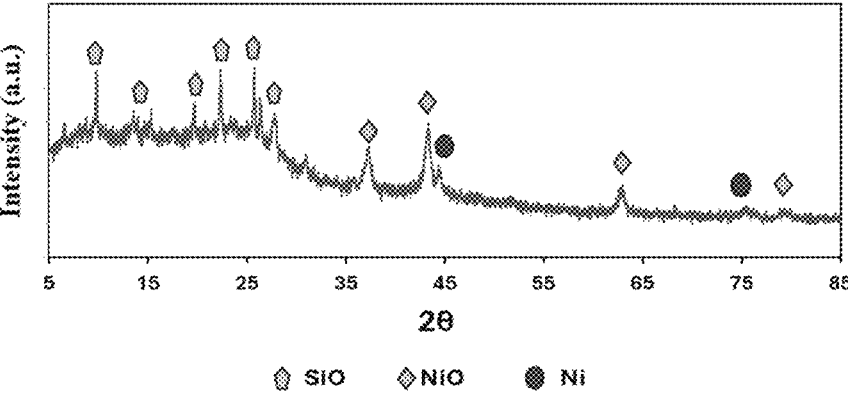

FIG. 6 illustrates the X-ray Diffraction (XRD) of hybrid-supported catalyst as per the present disclosure (Example 3).

FIG. 7 illustrates the Fourier Transform Infrared Spectroscopy (FTIR) of hybrid-supported catalyst as per the present disclosure (Example 3).

FIG. 8($a$) and FIG. 8($b$) illustrate the conversion percentage and the selectivity profile of hybrid-supported catalyst as per the present disclosure (Example 3), respectively.

FIG. 9($a$) illustrates the conversion of 1,3-butadiene (BD) changes with reaction temperature for hybrid-supported catalyst as per the present disclosure (Example 3), Comparative Example 1 and Comparative Example 2.

FIGS. 9($b$) to 9($d$) illustrate the selectivity of catalyst in Comparative Example 1 (NB), selectivity of catalyst of Comparative Example 2 (NZ) and selectivity of the catalyst in Example 2 (NZB) as per the present invention, respectively.

Figure 10:
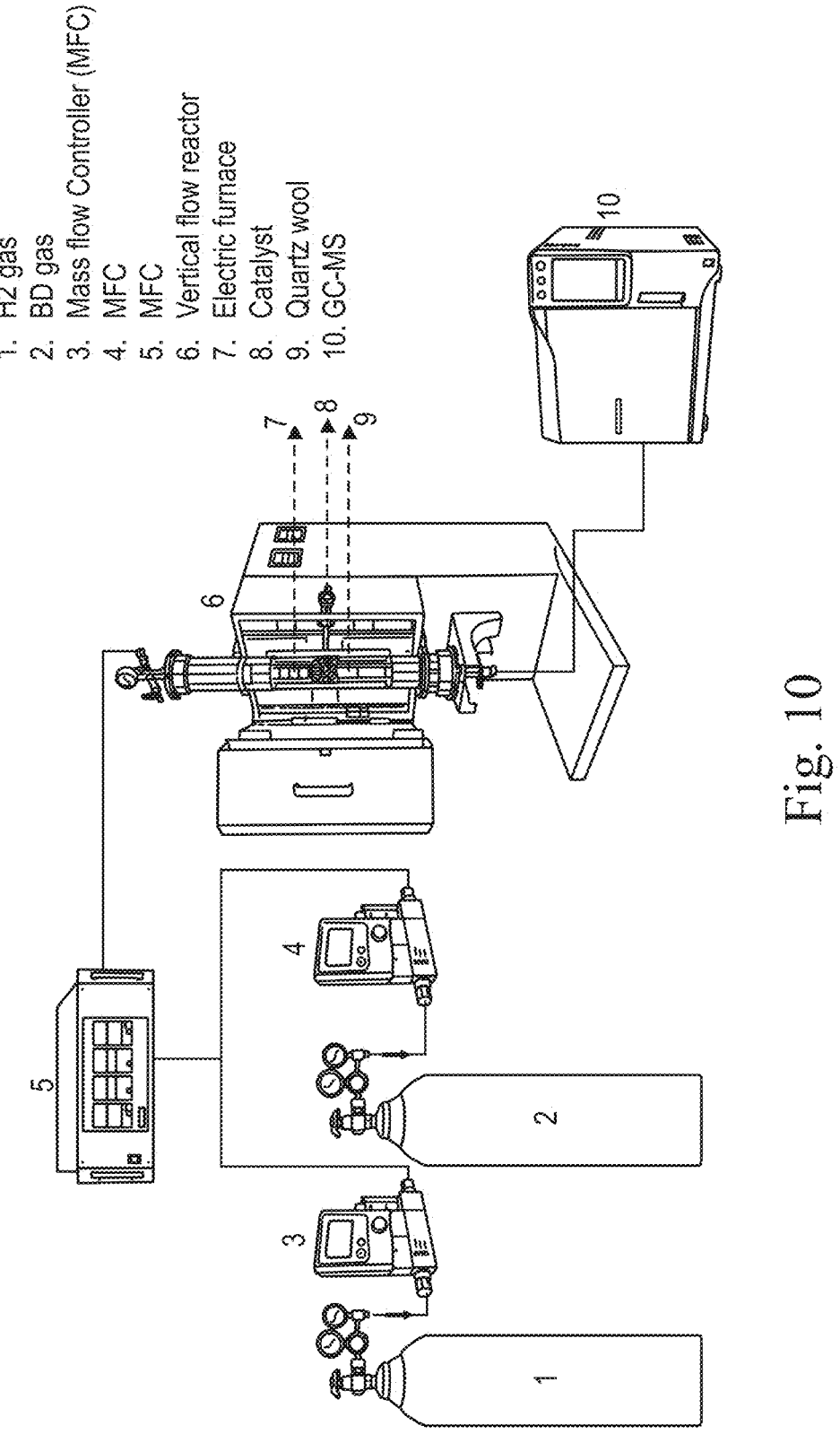

FIG. 10 illustrates the instrumental set up for hydrogenation of butadiene (BD).

DETAILED DESCRIPTION

The present disclosure has been developed to solve one or more of the problems described above, and provides a hybrid-supported catalyst, a process for preparing thereof and a method for hydrogenation of unsaturated hydrocarbon(s) in the presence of the hybrid-supported catalyst.

The objects of the present disclosure can be understood more readily by reference to the following description taken in connection with the accompanying Figures and Examples, all of which form a part of this disclosure.

At the very outset of the detailed description, it may be understood that the ensuing description only illustrates a particular form of this disclosure. However, such a particular form is only an exemplary embodiment, and without intending to imply any limitation on the scope of this disclosure. Accordingly, the description is to be understood as an exemplary embodiment and teaching of disclosure and not intended to be taken restrictively.

Before the present disclosure or methods of the present disclosure are described in greater detail, it is to be understood that the specific products, methods, processes, conditions or parameters, are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the 5 smaller ranges and are also encompassed within the methods, subject to any specifically excluded limit in the stated range.

Unless otherwise defined, all terms used in the disclosure, including technical and scientific terms, have meaning as commonly understood by one of ordinary skill in the art to which this disclosure belongs. By means of further guidance, term definitions are included for better understanding of the present disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

It must be noted that as used in this specification and the appended claims, the singular forms "a," "an" and "the" include plural referents unless the content clearly dictates otherwise.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, "about" can mean within one or more standard deviations, or within ±30%, 25%, 20%, 15%, 10% or 5% of the stated value.

As used herein, the terms "comprises", "comprising", or any other variations thereof, are intended to cover a non-exclusive inclusion, such that a method that comprises a list of acts does not include only those acts but may include other acts not expressly listed or inherent to such method. In other words, one or more acts in a method proceeded by "comprises . . . a" does not, without more constraints, preclude the existence of other acts or additional acts.

Reference throughout this specification to "certain embodiments", "further embodiments", "some embodiments", "one embodiment", "an embodiment", "a non-limiting embodiment", "an exemplary embodiment", "some instances", or "further instances", means that a particular feature, structure or characteristic described in connection with the embodiment may be included in at least one embodiment of the present disclosure. Thus, the appearances of the "certain embodiments", "further embodiments", "some embodiments", "one embodiment", "an embodiment", "a non-limiting embodiment", "an exemplary embodiment", "some instances", or "further instances", in various places throughout this specification may not necessarily all refer to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

The use of any and all examples, or exemplary language (e.g., "such as") provided with respect to certain embodiments herein is intended merely to better illustrate the disclosure and does not pose a limitation on the scope of the disclosure otherwise claimed.

The order in which the method is described is not intended to be construed as a limitation, and any number of the method blocks described may be combined in any order to implement the method. Additionally, individual blocks may be deleted from the methods without departing from the scope of the subject matter described herein.

As used herein, the terms 'include', 'have', 'comprise', 'contain' etc. or any form of said terms such as 'having', 'including', 'containing', 'comprising' or 'comprises' are inclusive and will be understood to imply the inclusion of a stated element, integer or step, or group of elements, integers or steps, but not the exclusion of any other element, integer or step, or group of elements, integers or steps.

The terms "process(es)" and "method(s)" are used interchangeably within this disclosure.

In one embodiment, the present disclosure provides a hybrid-supported catalyst. The hybrid-supported catalyst comprising:

a hybrid support comprising a silica containing material and a biochar; and a hydrogenation catalyst dispersed on the hybrid support.

The biochar for the purpose of the present disclosure may be any kind of biochar derived from biomass. Biomass can be selected from a variety of sources such as plant materials, food organic waste materials, agricultural waste materials, cellulosic materials, lignin containing material, any other naturally derived sources of carbon, or combination thereof. For example, a biomass includes without limitation one or more materials selected from the group consisting of date pit(s), date pit(s) waste, corn cobs, sawdust, wood chips, crop stalks, husks, straw, and any combination thereof. The biochar may present in at least 70 wt. % based on the total weight of the hybrid support. In an embodiments, the biochar is present in about 70 wt. % to about 75 wt. % based on the total weight of the hybrid-supported catalyst.

In an embodiment, biochar is derived from date pit(s), and/or date pit(s) waste. Thus, in certain embodiments, the present disclosure provides a hybrid-supported catalyst, comprising:

a hybrid support comprising a silica containing material and a biochar derived from date pit(s), and/or date pit(s) waste; and a hydrogenation catalyst dispersed on the hybrid support.

Date pits are a significant type of biomass waste found globally. The date seed is an interesting non-woody material, constituting about 10% of the date fruit, with a small cylindrical embryo embedded in a horny endosperm of cellulose and hemicellulose. Despite their high fiber content, date seeds are still considered as unwanted waste and are discarded or used as animal feed after the date meat is consumed. Middle Eastern and North African countries are major producers of dates, generating over 1 million tons of date seeds annually. By using a date pit-derived biochar, the hybrid-supported catalyst repurposes agricultural waste, contributing to circular economy principles.

The use of waste-derived biochar potentially offers significant cost savings in industrial hydrogenation processes. Thus, in an embodiment, the present disclosure provides an energy efficient, environmentally friendly, and cost-effective hybrid-supported catalyst.

In certain embodiments, the hybrid-supported catalyst of the present disclosure combines a biochar derived from biomass such as date pit(s) and/or date pit waste with (i) a silica containing material such as zeolite and (ii) a hydrogenation catalyst. This hybrid structure provides a synergistic effect not seen in traditional supported catalysts. The hybrid-supported catalyst of the present disclosure exhibits remarkable resistance to deactivation, maintaining high catalytic activity over extended periods without significant loss of performance.

In an embodiment, the hybrid-supported catalyst operates effectively at relatively low temperature (e.g., equal or less than 200° C.), potentially reducing energy costs in industrial applications. Thus, the hybrid-supported catalyst demonstrates high efficiency at temperature, significantly lower than conventional hydrogenation catalysts, offering substantial energy savings.

The silica containing material is present in an amount ranging from about 8 wt. % to about 15 wt. % based on the total weight of the hybrid-supported catalyst. In an embodiment, the silica containing material is selected from a group comprising zeolite, silica, silicalite, and a combination thereof. In an embodiment, the silica containing material has an average particle size of about 1 micron to about 50 micron.

In a specific embodiment, the silica containing material is zeolite. The zeolites are crystalline aluminosilicates with a characteristic porous structure made up of a three-dimensional network of $SiO_4$ and $AlO_4$ tetrahedra cross-linked by shared oxygen atoms with a variety of structures and silicon to aluminum contents. Suitable zeolites include, but not limited to, aluminosilicate zeolite composed of silicon and aluminum as constituent elements, aluminophosphate zeolite composed of aluminum and phosphorus, and silicoaluminophosphate zeolite composed of silicon, aluminum and phosphorus.

Thus, in certain embodiments, the present disclosure provides a hybrid-supported catalyst, comprising:

a hybrid support comprising a zeolite and a biochar derived from date pit(s), and/or date pit(s) waste; and a hydrogenation catalyst dispersed on the hybrid support.

In a specific embodiment, the zeolite is aluminosilicate zeolite.

The $SiO_2/Al_2O_3$ molar ratio in the aluminosilicate is not particularly limited but it is 10 or more. If the molar ratio is less than the lower limit above, rapid deactivation of the hydrogenation catalyst occurs. In some embodiments, the $SiO_2/Al_2O_3$ molar ratio is 206 or less. If the molar ratio exceeds this upper limit, the hydrogenation of unsaturated hydrocarbon may decrease.

In certain embodiments, the zeolite is mordenite. In an embodiment, the zeolite has an average pore size of about 1 Angstrom to about 7.1 Angstroms.

In an embodiment, the hydrogenation catalyst comprises a catalytically active metal selected from the group consisting of nickel, cobalt, iridium, molybdenum, osmium, palladium, platinum, ruthenium, tungsten, and mixtures thereof. In an embodiment, the hydrogenation catalyst comprises the catalytically active metal comprises nickel.

In an embodiment, the hydrogenation catalyst is present in an amount ranging from about 15 wt. % to about 20 wt. % based on the total weight of the hybrid-supported catalyst.

In an embodiment, the hydrogenation catalyst is uniformly dispersed on the hybrid support. The uniform dispersion of hydrogenation catalyst on the hybrid support enhances catalytic activity and stability.

In an embodiment, the catalytically active metal of the hydrogenation catalyst has an average particle size of about 1.3 nm to about 17 nm.

In an embodiment, the hybrid-supported catalyst comprises about 8 wt. % to about 15 wt. % of the silica containing material; about 70 wt. % to about 75 wt. % of the biochar; and about 15 wt. % to about 20 wt. % of the hydrogenation catalyst based on the total weight of the hybrid-supported catalyst. The biochar, zeolite, and hydrogenation catalyst in the hybrid-supported catalyst create a synergistic effect that enhances catalytic performance beyond what each component could achieve individually.

In an embodiment, the hybrid-supported catalyst comprises about 8 wt. % to about 15 wt. % of the zeolite; about 70 wt. % to about 75 wt. % of the biochar; and about 15 wt. % to about 20 wt. % of the hydrogenation catalyst based on the total weight of the hybrid-supported catalyst.

In an embodiment, the hybrid-supported catalyst has an average particle size of about 30 nm to about 35 nm.

In an embodiment, the hybrid-supported catalyst has a pore volume of about 0.015 cc/g to about 0.017 cc/g.

In an embodiment, the hybrid-supported catalyst has a BET surface area of about 90 $m^2/g$ to about 100 $m^2/g$.

Utility/Advantages of the Product/Hybrid-Supported Catalyst

The hybrid-supported catalyst of the present disclosure demonstrates exceptional resistance to deactivation, potentially revolutionizing long-term industrial applications. It operates efficiently at much lower temperatures (equal or less than 200° C.), promising substantial energy savings. The hybrid-supported catalyst consistently achieves at least 99% conversion, enhancing product purity and process efficiency.

The present disclosure uniquely leverages date pit waste, transforming it into a valuable catalytic material. Further, the integration of silica containing material within the biochar, coupled with precisely dispersed catalytically active metal creates a synergistic effect. This synergy enhances catalytic activity beyond what each component could achieve individually.

The present disclosure also provides a process for preparing a hybrid-supported catalyst. The process comprises the steps of:

a) adding a solution comprising a hydrogenation catalyst to a biochar to get a suspension;

b) adding a solution of a silica containing material to the suspension with constant stirring to obtain a wet hybrid-supported catalyst;

c) drying the wet hybrid-supported catalyst; and d) calcining the dried hybrid-supported catalyst.

In an embodiment, step a) and b) of said process are carried out at room temperature.

In an embodiment, in step b) of said process, the solution of a silica containing material is added to the suspension with constant stirring for about 5 mins to 90 mins.

In an embodiment, in step b) of said process, the solution of a silica containing material is added to the suspension with constant stirring for about 15 mins to 60 mins.

In an embodiment, in step b) of said process, the solution of a silica containing material is added to the suspension with constant stirring for about 15 mins to 45 mins.

In an embodiment, the wet hybrid-supported catalyst is dried at temperature of 40° C. to 150° C.

In an embodiment, the wet hybrid-supported catalyst is dried at temperature of 60° C. to 130° C.

In an embodiment, the dried hybrid-supported catalyst is calcined at temperature of 350° C. to 600° C.

In an embodiment, the dried hybrid-supported catalyst is calcined at temperature of 400° C. to 500° C.

In certain embodiments, the silica containing material, the biochar, and the hydrogenation catalyst are same as defined in any of the preceding embodiments.

In an embodiment, the silica containing material is zeolite, and the biochar is derived from date pit(s) and/or date pit waste.

In an embodiment, the silica containing material is silica, and the biochar is derived from date pit(s) and/or date pit waste.

In an embodiment, the biochar from date pit(s) and/or date pit(s) waste is prepared by pyrolysis of date pit(s) and/or date pit(s) waste in a reactor.

Suitable reactor includes, but not limited to, a flow reactor, and horizontal quartz tube reactor.

In certain embodiments of the process, the biochar is present in an amount ranging from about 70 wt. % to about 75 wt. % based on the total weight of the hybrid-supported catalyst.

In certain embodiments of the process, the silica containing material is present in an amount ranging from about 8 wt. % to about 15 wt. % based on the total weight of the hybrid-supported catalyst.

In certain embodiments of the process, the hydrogenation catalyst is present in amount ranging from about 15 wt. % to about 20 wt. % based on the total weight of the hybrid-supported catalyst.

In certain embodiments of the process, the hydrogenation catalyst comprises a catalytically active metal selected from the group consisting of nickel (Ni), cobalt, iridium, molybdenum, osmium, palladium, platinum, ruthenium, tungsten, and mixtures thereof. In an embodiment, the catalytically active metal is nickel.

In certain embodiments of the process, the catalytically active metal of the hydrogenation catalyst has an average particle size of about 1.3 nm to about 17 nm.

In certain embodiments of the process, the hydrogenation catalyst is uniformly dispersed on the hybrid support. The uniform dispersion of hydrogenation catalyst on the hybrid support, enhances catalytic activity and stability. The uniform dispersion of the hydrogenation catalyst on the hybrid support is carried out by method, but not limited to wet impregnation method, and the elemental distribution was analyzed using SEM-EDS mapping.

In an embodiment, the process of preparing the hybrid-supported catalyst comprises about 8 wt. % to about 15 wt. % of the silica containing material; about 70 wt. % to about 75 wt. % of the biochar; and about 15 wt. % to about 20 wt. % of the hydrogenation catalyst based on the total weight of hybrid-supported catalyst. The silica containing material, biochar, and hydrogenation catalyst in the hybrid-supported catalyst create a synergistic effect that enhances catalytic performance beyond what each component could achieve individually.

The present disclosure further provides a method for hydrogenation of an unsaturated hydrocarbon. The method comprises contacting unsaturated hydrocarbon with hydrogen in the presence of a hybrid-supported catalyst; wherein the hybrid support comprises a silica containing material, a biochar; and a hydrogenation catalyst.

In certain embodiments, the present disclosure provides a method for hydrogenation of an unsaturated hydrocarbon comprising contacting the unsaturated hydrocarbon with hydrogen in the presence of a hybrid-supported catalyst; wherein the hybrid-supported catalyst is as defined in any of the preceding embodiments. In certain embodiments, the hydrogenation is a selective hydrogenation.

This process addresses one or more limitations associated with existing methods/processes and provides a cost-effective process employing biochar derived from unused waste resulting in high yield of selective hydrogenated product.

In one embodiment of the present disclosure, a cost-effective and efficient process is provided for the production of a butene from selective hydrogenation of butadiene by utilizing biochar derived from date pit(s) and/or date pit(s) waste.

In certain embodiments, the present disclosure leverages the unique process of enhancing yield of butene by utilizing date pit(s) and/or date pit(s) waste.

In certain embodiments, the method for hydrogenation of an unsaturated hydrocarbon comprises: contacting unsaturated hydrocarbon with hydrogen in the presence of a hybrid-supported catalyst at a temperature of 150° C. to 350° C. and at atmospheric pressure; wherein the hybrid-supported catalyst, comprises: (i) a hybrid support comprising silica containing material and a biochar; and (ii) a hydrogenation catalyst dispersed on the hybrid support. The silica containing material, the biochar, and the hydrogenation catalyst are same as defined in any of the preceding embodiments.

In an embodiment, the method for selective hydrogenation of an unsaturated hydrocarbon comprises contacting unsaturated hydrocarbon with hydrogen in a reactor in the presence of a hybrid-supported catalyst; wherein the ratio of unsaturated hydrocarbon to hydrogen ranges from about 1:3.8 to about 1:4.2. The form of the reactor used is not particularly limited, but a continuous fixed-bed reactor or a fluidized-bed reactor is usually selected. A fluidized-bed reactor is preferred.

In an embodiment, the unsaturated hydrocarbon is selected from a group comprising butadiene, Isoprene, 1,3-pentadiene, 1,3-hexadiene and cyclopentadiene.

In an embodiment, the unsaturated hydrocarbon is butadiene.

In an embodiment, the hydrogenation of butadiene in the presence of the hybrid-supported catalyst results selective hydrogenation, can obtain 100% olefin selectivity and completely avoid generating low-value hydrogenation product such as n-butane. The obtained hydrogenated product is rich in high-added value product such as 1-butene. In addition, the hybrid-supported catalyst provided by the disclosure has good service life.

The present disclosure achieves 100% conversion of butadiene to the olefin, addressing critical health and environmental concerns associated with butadiene: Butadiene is a known human carcinogen, linked to increased risk of leukemia and other cancers. Its exposure can cause respiratory irritation and potentially serious lung damage. Butadiene contributes to air pollution and smog formation. Industrial workers face significant exposure risks during production and handling. Butadiene is highly flammable, posing fire and explosion hazards in industrial settings. It can contribute to stratospheric ozone depletion. By achieving complete conversion, hybrid-supported catalyst of the present disclosure significantly mitigates these risks, enhancing workplace safety, reducing environmental impact, and improving overall process efficiency in industries reliant on butadiene. By enabling complete conversion of toxic butadiene and utilizing waste materials, the catalyst offers significant environmental benefits.

The present invention provides the energy efficient, environmentally friendly, deactivation resistant and/or cost-effective hybrid-supported catalyst with improved catalytic activity.

The present disclosure provides a scalable and cost-effective solution for large-scale applications. The importance of this disclosure lies in its potential to significantly reduce energy consumption in hydrogenation processes, highly deactivation resistance, extend catalyst lifespan, reducing operational costs and downtime, improve product quality through complete conversion, a sustainable solution by upcycling agricultural waste, potentially apply to a wide range of hydrogenation reactions beyond butadiene conversion.

The present disclosure addresses the critical issues of the conventionally known supported catalyst and in hydrogenation of unsaturated hydrocarbon. Thus, the present disclosure could lead to more efficient, sustainable, and economical processes in the petrochemical industry and beyond. The unique combination of high performance, sustainability, and potential for wide-ranging applications sets this catalyst apart from existing solutions in the field.

Certain specific aspects and embodiments of the present application will be explained in greater detail with reference to the following examples, which are provided only for purposes of illustration and should not be construed as limiting the scope of the application in any manner. While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

EXAMPLES

The following examples are given by way of illustration of the working of the disclosure in actual practice and therefore should not be construed to limit the scope of the present disclosure in any way.

Physical Property Measurement Method

The workability and effectiveness of the disclosed hybrid support catalyst have been thoroughly demonstrated through a comprehensive set of characterization techniques and performance tests are as mentioned below.

Structural and Compositional Analysis:

Scanning Electron Microscopy (SEM): The morphology of the hybrid-supported catalyst is revealed by Energy Dispersive X-ray Spectroscopy (EDS) mapping that confirmed the distribution of silica containing material such as zeolite and catalytically active metal such as nickel on the biochar.

X-ray Diffraction (XRD)): Identified the crystalline phases present in the hybrid-supported catalyst.

Fourier Transform Infrared Spectroscopy (FTIR): Provided information on the surface functional groups on the hybrid-supported catalyst.

Surface and Thermal Properties

Brunauer-Emmett-Teller (BET) analysis: BET surface area and pore volume of the hybrid-supported catalyst samples were determined from a Micromeritics ChemiSorb 2750 instrument. The sample holder was thoroughly cleaned and dried before the sample was accurately weighed (0.5 g) and loaded. Prior to analysis, the sample underwent a degassing step where it was heated to 300° C. to remove moisture and adsorbed contaminants, then allowed to cool to room temperature. A gas mixture of $N_2$ with helium used for multipoint surface area analysis. The room temperature was recorded at 27° C. and the sample holder was cooled to liquid nitrogen temperature. The atmospheric pressure was 760 mmHg. The specific surface area was then calculated using the equations. For quality control purposes, a single-point analysis was also conducted.

The multipoint surface area measurement commenced with the lowest nitrogen concentration, from 10%. The corresponding pressure readings were recorded, and the nitrogen concentration gradually increased to 40%. Three to four measurements were taken at different relative pressures (P/Po) to ensure accurate results. During each measurement point, essential parameters including gas volume, room temperature, atmospheric pressure, saturation pressure, and relative pressure (P/Po) were recorded.

Thermogravimetric Analysis (TGA): Assessed the thermal stability of the catalyst. TGA analysis is done by SDT 650 from TA instruments. The thermal stability and composition are analyzed with a ramp change of 10° C. $min^{-1}$. The thermal stability checked up to 400° C. and the catalyst is thermally stable with no considerable mass lose noted.

Catalytic Property Analysis

Temperature Programmed Reduction (TPR): Evaluated the reducibility of the catalytically active metal such as nickel. The TPR studies were conducted using a Micromeritics ChemiSorb 2750 instrument. The TPR tests were performed by heating the samples from room temperature to 600° C. at a rate of 10° C. per minute, under a total flow of 25 ml/min of a gas mixture containing 10% $H_2$ in argon. Prior to the TPR experiments, the fresh catalysts of 30 mg were pretreated at 200° C. for 1 hour under a flow of Argon gas to remove water and other contaminants present in the samples.

Temperature Programmed Desorption (TPD): Analyzed the dispersion percentage of catalytically active metal. The $H_2$-TPD technique was employed to investigate the strength of the binding between hydrogen and the active nickel sites on the catalyst surface. In this experiment, a catalyst sample (30 mg) underwent pretreatment under a gas mixture of 10% $H_2$ and 90% Ar, at 600° C. for 90 minutes. After this pretreatment process, the sample was cooled down to 50° C. under an argon flow for removing any weakly adsorbed $H_2$ species from the catalyst surface. Then, the sample was heated from 50° C. to 700° C. at a rate of 10° C./min under an argon flow of 30 mL/min. The desorbed $H_2$ species were detected using a thermal conductivity detector (TCD). Then the $H_2$-TPD profile was constructed by plotting the desorbed $H_2$ signal against temperature.

To determine the dispersion of active metal sites on the catalyst surface, the information from the $H_2$-TPR analysis was also utilized. The number of surface nickel sites per unit mass of the catalyst was determined by means of $H_2$-TPD. The dispersion of nickel was calculated based on the volume of chemisorbed $H_2$, using a simplified equations that relate the amount of chemisorbed $H_2$ to the number of exposed nickel atoms on the catalyst surface.

Figure 1:
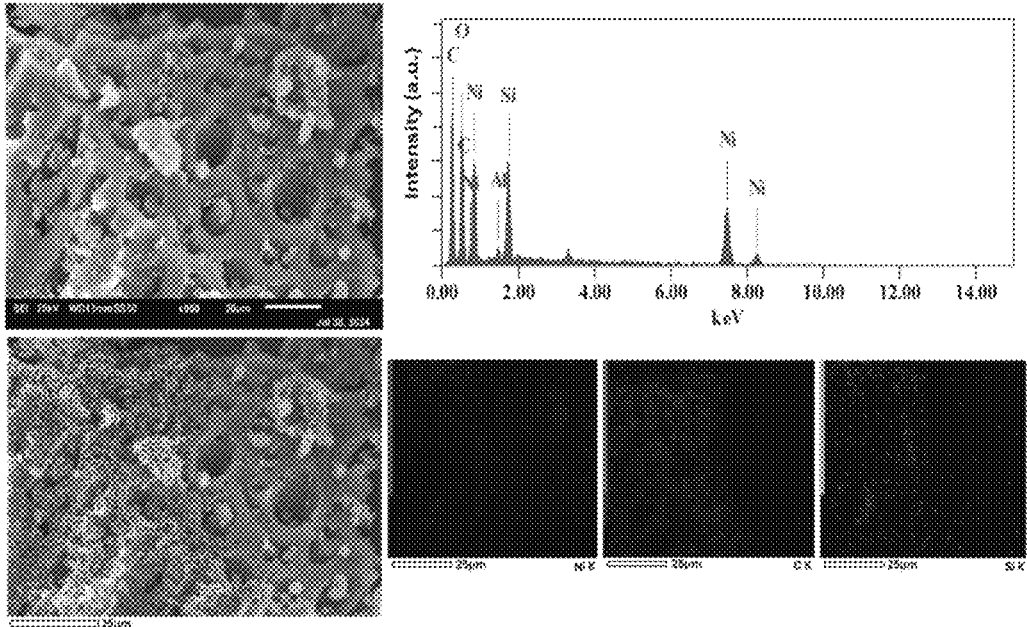
Figure 2:
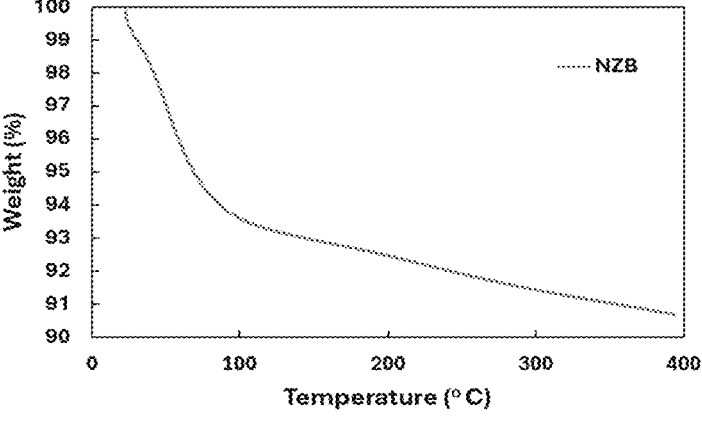
FIG. 2 illustrates the Thermogravimetric Analysis (TGA) of hybrid-supported catalyst as per the present disclosure (Example 3).
Figure 3:
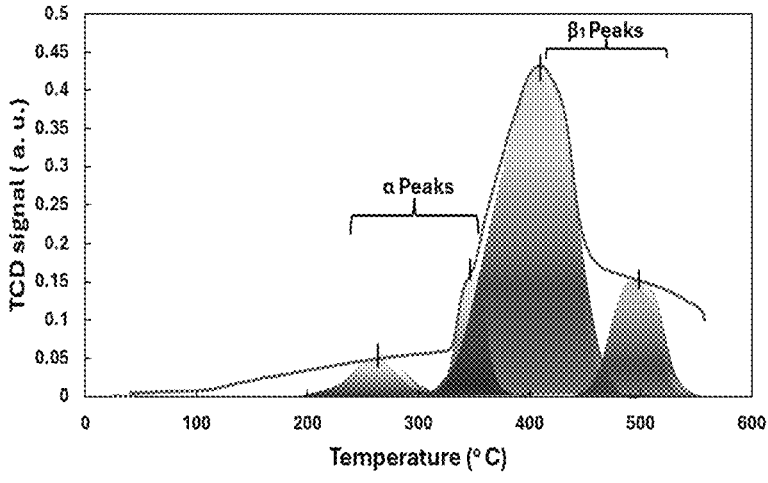
FIG. 3 illustrates the Temperature Programmed Reduction (TPR) of hybrid-supported catalyst as per the present disclosure (Example 3).
Figure 4:
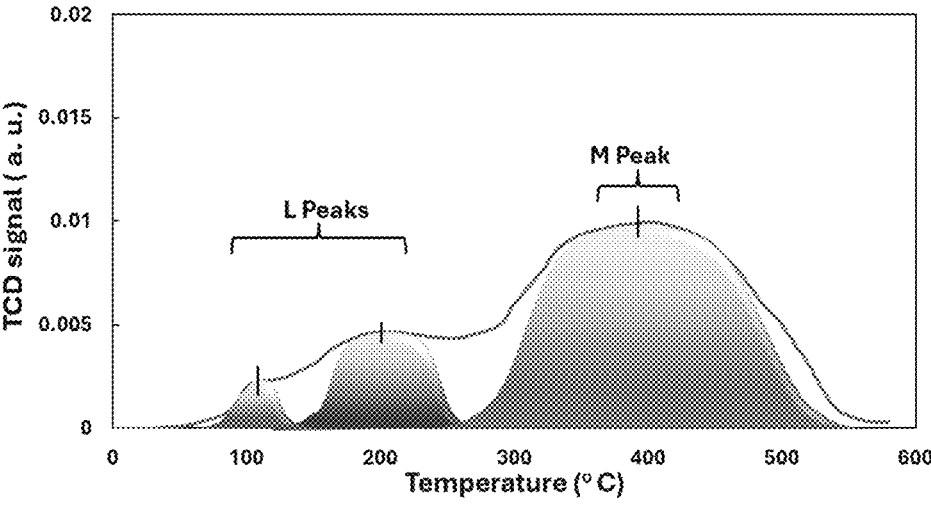
FIG. 4 illustrates the Temperature Programmed Desorption (TPD) of hybrid-supported catalyst as per the present disclosure (Example 3).
Figure 5A:
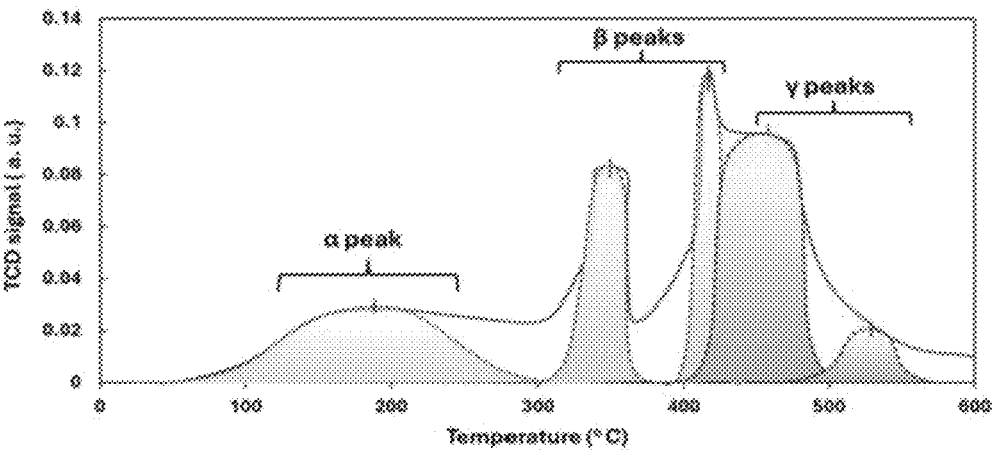
Figure 5B:
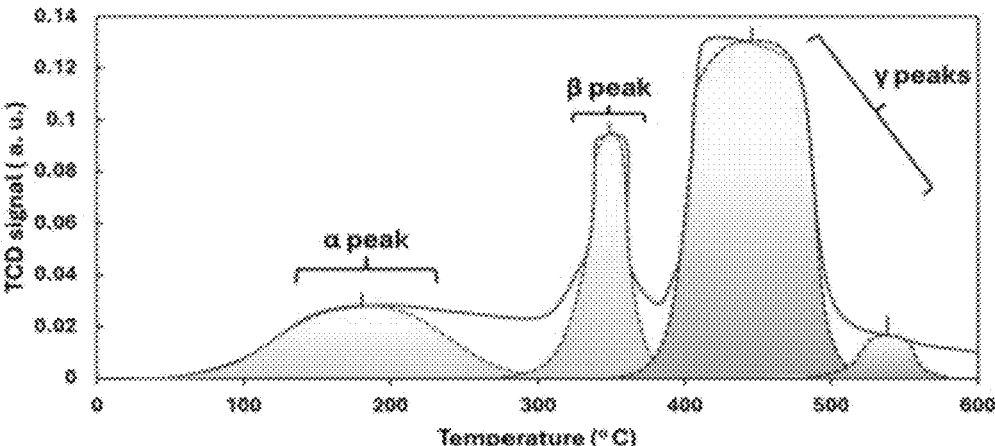

Temperature Programmed Oxidation (TPO)): Assessed the deactivation of hybrid-supported catalyst. The Micromeritics ChemiSorb 2750 device was used in the TPO study. Heated the samples from room temperature to 600° C. at a rate of 10° C. per minute for this test. The whole flow of the gas mixture (20% oxygen in argon) maintained at 25 ml/min. Before the TPO tests, the hybrid-supported catalyst was heated to 200° C. for an hour under a flow of Argon gas to get rid of any water or other pollutants that were in the samples. By looking at the TPO profiles of both fresh and used hybrid-supported catalyst, can learn about how much deactivated. $\alpha$, $\beta$, and $\gamma$, are used to show the three main types of peaks. FIG. 5(a) and FIG. 5(b) show that each one corresponds to a different type of carbon deposit.

The hybrid-supported catalyst was synthesized as follows:

Example 1: Synthesis of Biochar from Date Pit(s)

Biochar was prepared by pyrolysis of the data pit(s). The date pit powder was carefully dried overnight in an oven which is set to a temperature of 100° C. to get rid of all the water. Thereafter, the dried powder was calcined at temperature 450° C. for one hour in a horizontal quartz tube reactor with a controlled flow of 100 ml/min of nitrogen gas. This process decomposed the date pit and created biochar.

Example 2: The Hybrid-Supported Catalyst as Per the Present Disclosure

Wet impregnation method was used to prepare the hybrid-supported catalyst. 2.232 g $Ni(NO_3)_2 \cdot 6H_2O$ was dissolved in distilled water (20 ml). This solution was added dropwise to the biochar (2.25 g) prepared in Example 1, followed by dropwise addition of 10% zeolite (0.3 g dissolved in 1 ml distilled water) with constant stirring for about 30 minutes to get the wet catalyst. The wet hybrid-supported catalyst was then dried in an oven for 16 hours at 100° C. and then calcined for 3 hours at 500° C. to get the hybrid-supported catalyst (Nickel zeolite biochar, NZB). This catalyst demonstrated the particle size of 34.81 nm, pore volume of 0.01663 $cm^2/g$ and the BET surface area of 97.38 $m^2/g$.

Example 3: Hydrogenation of 1,3-butadiene (BD)

The hydrogenation of 1,3-butadiene was carried out in the presence of the hybrid-supported catalyst of Example 2 at a temperature of 150-350° cand at atmospheric pressure in a continuous-flow fixed bed reaction system as shown in FIG. 10. This reactor consists of a quartz tube inside an electric furnace that could control the temperature.

The hybrid-supported catalyst of Example 2 (0.8 grams) was put in the tube, held in place by quartz wool. The helium gas (50 mL/min) passed through the catalyst at 400° C. for 30 minutes to remove the volatile content (such as moisture). Then, the catalyst was reduced with a mixture of 5% $H_2$ and 95% He gases at 500° C. for 2 hours.

Hydrogen gas and 1,3-butadiene gas (BD) flowed through the catalyst at a rate of 90 mL/min ($H_2$: BD=4.0, weight hourly space velocity=9,000 mL $g^{-1}h^{-1}$). The products of the hydrogenation were analyzed with the aid of a Gas Chromatography (Model 2030, Shimadzu) with a 19,778 Rt-Alumina BOND/MAPD 50 m 0.53 mm ID 10 μm column, connected online to the reactor. The utilized column effectively separate all potential C3-C4 species and their isomers as shown in FIG. 9(a).

Comparative Example 1

Hydrogenation of 1,3-butadiene (BD) is carried similar to Example 3, except nickel biochar catalyst (NB) is used instead of the hybrid-supported catalyst of Example 2. The NB catalyst showed a gradual increase in conversion, peaking at 97% at 250° C. before severe deactivation with TOF of 0.0189 $s^{-1}$ as shown in FIG. 9(a).

Comparative Example 2

Hydrogenation of 1,3-butadiene (BD) is carried similar to Example 3, except nickel zeolite catalyst (NZ) is used instead of the hybrid-supported catalyst of Example 2. The NZ catalyst reached 98% conversion at 200° C. and full conversion at 250° C., with TOF of 0.042 $s^{-1}$ but experienced significant deactivation at higher temperatures as shown in FIG. 9(a). In the above Example and Comparative Examples, the catalytic performance of the above three nickel-based catalysts: nickel zeolite biochar (NZB) (Example 3) as per the present disclosure, nickel biochar (NB) catalyst (Comparative Example 1) and nickel zeolite (NZ) catalyst (Comparative Example 2) in the hydrogenation of 1,3-butadiene (BD) was extensively examined at a temperature range of 150-350° C.

The Hybrid-supported catalyst (NZB) of Example 3 demonstrated remarkable activity and stability, achieving 100% conversion at 200° C. and maintaining this complete conversion up to 350° C. as shown in FIG. 8(a). Thus, the combination of biochar, zeolite, and nickel creates a synergistic effect that enhances catalytic performance beyond what each component could achieve individually.

FIG. 9(a) shows how the conversion of BD changes with reaction temperature for all three catalysts. FIG. 9(a) clearly shows that the hybrid-supported catalyst of Example 3 showed better performance than the usual NZ and NB catalysts. The NZ catalyst reached 98% conversion at 200° C. and full conversion at 250° C. But they experienced significant deactivation at higher temperatures. Similarly, the NB catalyst showed a gradual increase in conversion, peaking at 97% at 250° C. before severe deactivation. In striking contrast, the NZB catalyst as per the present disclosure demonstrated remarkable activity and stability, achieving 100% conversion at just 200° C. and maintaining this complete conversion up to 350° C. Thus, the hybrid-supported catalyst according to the present disclosure shows good deactivation resistance at the temperature range 200° C. to 350° C. and represents a significant advancement in catalyst for selective hydrogenation reactions.

These experimental data and characterization result collectively demonstrate the unique structure of the hybrid support catalyst of the present disclosure, its thermal and chemical stability, and its exceptional performance in the hydrogenation of butadiene with 100% conversion rate and resistance to deactivation.

The invention claimed is:

1. A hybrid-supported catalyst, comprising:
a hybrid support comprising silica containing material and a biochar; and
a hydrogenation catalyst dispersed on the hybrid support, wherein the silica containing material is selected from the group consisting of zeolite, silicalite, and a combination thereof, and
wherein, based on the total weight of the hybrid-supported catalyst:
the silica containing material is present in an amount ranging from about 8 wt. % to about 15 wt. %, and
the biochar is present in an amount ranging from about 70 wt. % to about 75 wt. %.

2. The hybrid-supported catalyst as claimed in claim 1, wherein the biochar is derived from a biomass.

3. The hybrid-supported catalyst as claimed in claim 2, wherein the biomass is date pit(s) and/or date pit(s) waste.

4. The hybrid-supported catalyst as claimed in claim 1, wherein the hydrogenation catalyst is present in an amount ranging from about 15 wt. % to about 20 wt. % based on the total weight of the hybrid-supported catalyst.

5. The hybrid-supported catalyst as claimed in claim 1, wherein the silica containing material is zeolite.

6. The hybrid-supported catalyst as claimed in claim 1, wherein the hydrogenation catalyst comprises a catalytically active metal selected from the group consisting of nickel (Ni), cobalt, iridium, molybdenum, osmium, palladium, platinum, ruthenium, tungsten, and mixtures thereof.

7. The hybrid-supported catalyst as claimed in claim 6, wherein the catalytically active metal is nickel.

8. The hybrid-supported catalyst as claimed in claim 1, wherein the hydrogenation catalyst is uniformly dispersed on the hybrid support.

9. The hybrid-supported catalyst as claimed in claim 1, wherein the hybrid-supported catalyst has an average particle size of about 30 nm to about 35 nm.

10. The hybrid-supported catalyst as claimed in claim 1, wherein the hybrid-supported catalyst has a pore volume of 0.015 cc/g±10% to 0.017 cc/g±10%.

11. A process for preparing the hybrid-supported catalyst of claim 1, comprising the steps of:
a) adding a solution comprising the hydrogenation catalyst to the biochar to get a suspension;
b) adding a solution of the silica containing material to the suspension with constant stirring to obtain a wet hybrid-supported catalyst;
c) drying the wet hybrid-supported catalyst; and
d) calcining the dried hybrid-supported catalyst to obtain the hybrid-supported catalyst.

12. The process as claimed in claim 11, wherein the biochar is derived from date pit(s) and/or date pit(s) waste.

13. The process as claimed in claim 12, wherein the biochar from date pit(s) and/or date pit(s) waste is prepared by pyrolysis of date pit(s) and/or date pit(s) waste in a reactor.

14. A method for hydrogenation of unsaturated hydrocarbon, comprising contacting the unsaturated hydrocarbon with hydrogen in the presence of a hybrid-supported catalyst as defined in claim 1.

15. The method as claimed in claim 14, wherein the unsaturated hydrocarbon is selected from the group consisting of butadiene, Isoprene, 1,3-pentadiene, 1,3-hexadiene, and cyclopentadiene.

16. The method as claimed in claim 14, wherein the method results in butene as the main product when the olefinic hydrocarbon is butadiene.

17. The hybrid-supported catalyst as claimed in claim 1, wherein:
the silica containing material is zeolite, and
the biochar is derived from date pit(s) and/or date pit(s) waste.

18. The hybrid-supported catalyst as claimed in claim 17, wherein the catalytically active metal is nickel.

19. The hybrid-supported catalyst as claimed in claim 18, wherein the zeolite is mordenite.

* * * * *